United States Patent [19]

Nettekoven

[11] 4,450,710

[45] May 29, 1984

[54] DEVICE FOR TESTING HEART VALVE PROSTHESES

[75] Inventor: William S. Nettekoven, White Bear Lake, Minn.

[73] Assignee: Medtronic, Inc., Minneapolis, Minn.

[21] Appl. No.: 310,467

[22] Filed: Oct. 13, 1981

[51] Int. Cl.³ .............................................. G01M 19/00
[52] U.S. Cl. ........................................... 73/37; 73/168
[58] Field of Search ........................ 73/37, 38, 168, 12

[56] References Cited

U.S. PATENT DOCUMENTS 3,962,906 6/1976 Heitmann et al. ...................... 73/38

OTHER PUBLICATIONS

Article entitled, "In Vitro Assessment of Mitral Valve Protheses", J. Thorac Cardio Surg., 79:680–688, 1980.
Article entitled, "In Vitro Hydrodynamic Comparison of Mitral Valve Bioprostheses", Cardiovascular Surgery, 1978, Supp. 1, Cir., vol. 60, No. 2, Aug. 1979.
Article entitled, The New Tilting Disc Cardiac Valve Prostheses, submitted to J. Thorac Cardio Surg. by Lawrence N. Scotten et al., pp. 1–23.
Article entitled, Pressure Drops Across Prosthetic Aortic Heart Valves Under Steady and Pulsatile Flow–In Vitro Measurements, J. Biomechanics, vol. 12, pp. 153–164, 1979.
Article entitled, "A Method of Measuring the Mean Pressure Gradient Across Prosthetic Heart Valves under In Vitro Pulsatile Flow Conditions", Medical Instrumentation, vol. 11, No. 2, pp. 110–113, Mar.–Apr. 1977.
Article entitled, The Lillehei–Kaster Pivoting Disc Aortic Prosthesis and A Comparative Study of Its Pulsatile Flow Characteristics with Four Other Prostheses, Trans. Amer. Soc. Artif. Int. Organs, vol. XVI, pp. 233–243, 1970.

Primary Examiner—James J. Gill
Attorney, Agent, or Firm—Schroeder, Siegfried, Vidas & Arrett

[57] ABSTRACT

A device for hydrodynamic, in vitro testing of heart valve prostheses. The device has a flow channel in which a flow of desired characteristics is induced. The flow channel includes a test fixture for supporting a prosthesis to be tested in a desired orientation within the flow. In a preferred embodiment, the test fixture includes first and second chambers spaced from each other along the flow channel and a shuttle intermediate the chambers which is movable between at least first and second positions. The shuttle includes at least one support for a heart valve prosthesis and selectively positions that prosthesis in the desired orientation within the flow by movement between the first and second positions. The shuttle may carry two or more heart valve prostheses to alternatively positioned one of them within the flow by movement of the shuttle. The chambers may be movable relative to each other to facilitate the establishment of static and dynamic seals of the flow channel between each of the chambers and the shuttle.

18 Claims, 4 Drawing Figures

DEVICE FOR TESTING HEART VALVE PROSTHESES

DESCRIPTION

BACKGROUND OF PRIOR ART

Heart valve prostheses of many types are known to the prior art. The in vitro testing of such valves for such purposes as design evaluation, comparison of different designs and production control is an obvious necessity. For these purposes, various flow characteristics have been employed such as steady, pulsatile, etc.

Typical devices or systems for hydrodynamic, in vitro testing of heart valve prostheses include a flow channel and a mechanism for inducing a flow of desired characteristics within that channel. A test fixture or station is provided within a flow channel and often includes a portion having a configuration that simulates that portion of the heart and/or vascular system with which the prosthesis to be tested is to be associated. Typically, the test fixture is assembled of multiple parts secured to each other and the remainder of the testing system by fastening devices which require a great deal of set up and take down time, relative to the testing time itself. This is true even when the new valve prosthesis to be tested is identical to the previously tested valve prosthesis.

BRIEF SUMMARY OF INVENTION

The present invention provides a device that facilitates the hydrodynamic, in vitro testing of heart valve prostheses and, particularly, the substitution of one valve prostheses for another within the testing apparatus. The present invention provides a test fixture within the flow channel of the testing apparatus, the test fixture being formed of first and second chambers spaced from each other along the flow channel with a shuttle intermediate the chambers, the shuttle being movable between at least first and second positions. The shuttle supports one or more heart valve prostheses and selectively positions a prosthesis in the desired orientation within the flow by movement between the first and second positions. When multiple prostheses are supported, they may be alternatively positioned within the flow by movement of the shuttle.

In a preferred embodiment, the shuttle is formed as a slide including a recess for each prosthesis to be supported. Each recess has a flow aperture which may be positioned in line with the flow channel by movement of the slide. A second recess overlies the prosthesis aperture and a collar positioned within the second recess engages the prosthesis to maintain it within its associated recess. The chambers may be movable relative to each other to establish static and dynamic seals between each of the chambers and the slide while sealing rings may be employed to enhance the sealing characteristics.

DETAILED DESCRIPTION OF INVENTION

Figure 1:
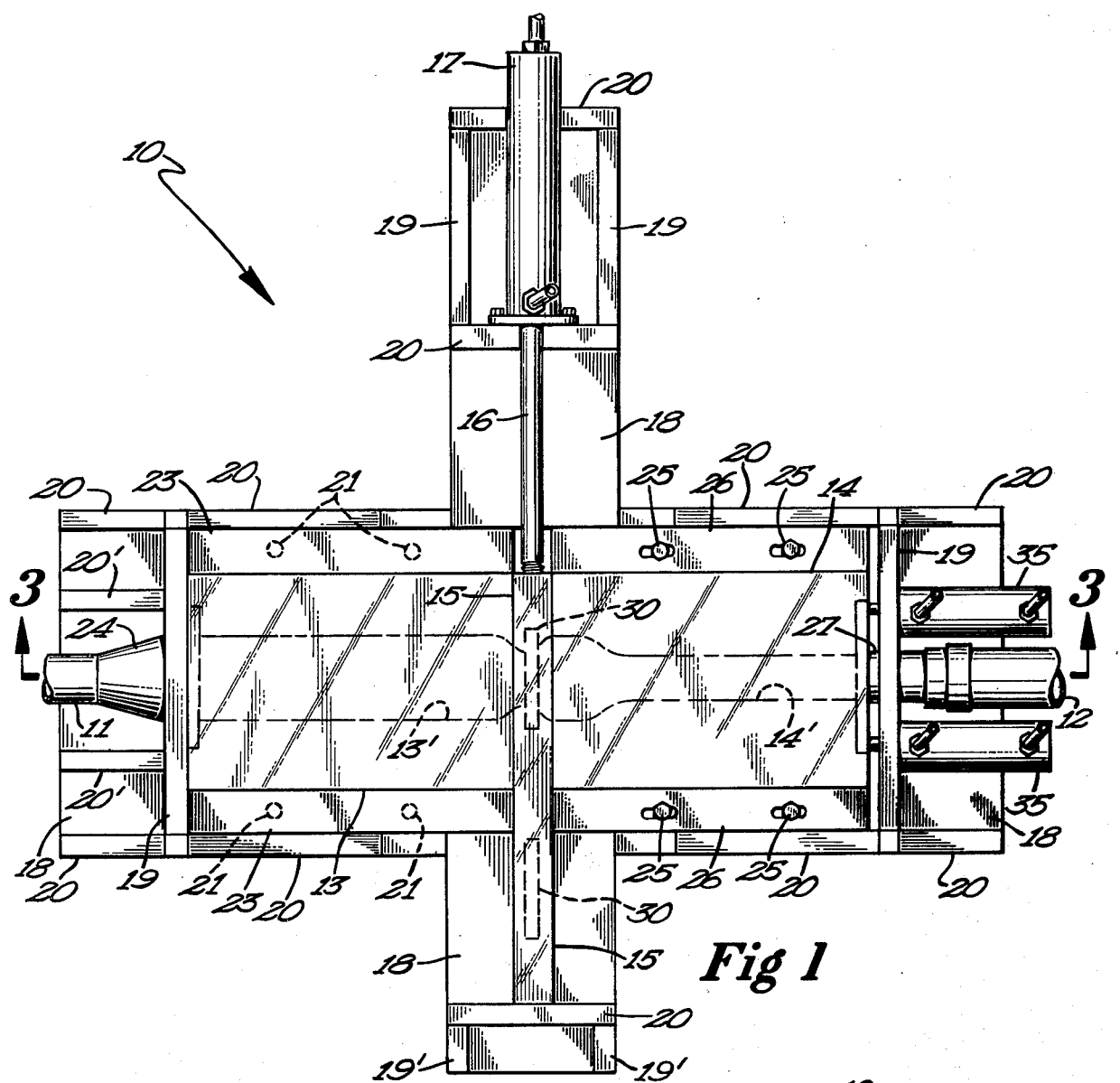
FIG. 1 is a top view of a preferred embodiment of a test fixture used in carrying out the present invention.

Referring now to FIG. 1, there is shown generally at 10 a test fixture in accordance with the present invention that may be advantageously employed in a system for hydrodynamic, in vitro testing of heart valve prostheses. As noted briefly above, such systems typically include a flow channel and a mechanism for establishing a flow of described characteristics within that channel. The test fixture 10 illustrated in the figures is interconnected with the system flow channel, forming a part thereof. Typically, the flow channel is formed largely of a clear plastic tubing such as Lucite which are indicated at stubs 11 and 12 in the figures. Except for its interconnection with the test fixture of the present invention, the system flow channel and flow inducing mechanism form no part of the present invention.

Figure 2:
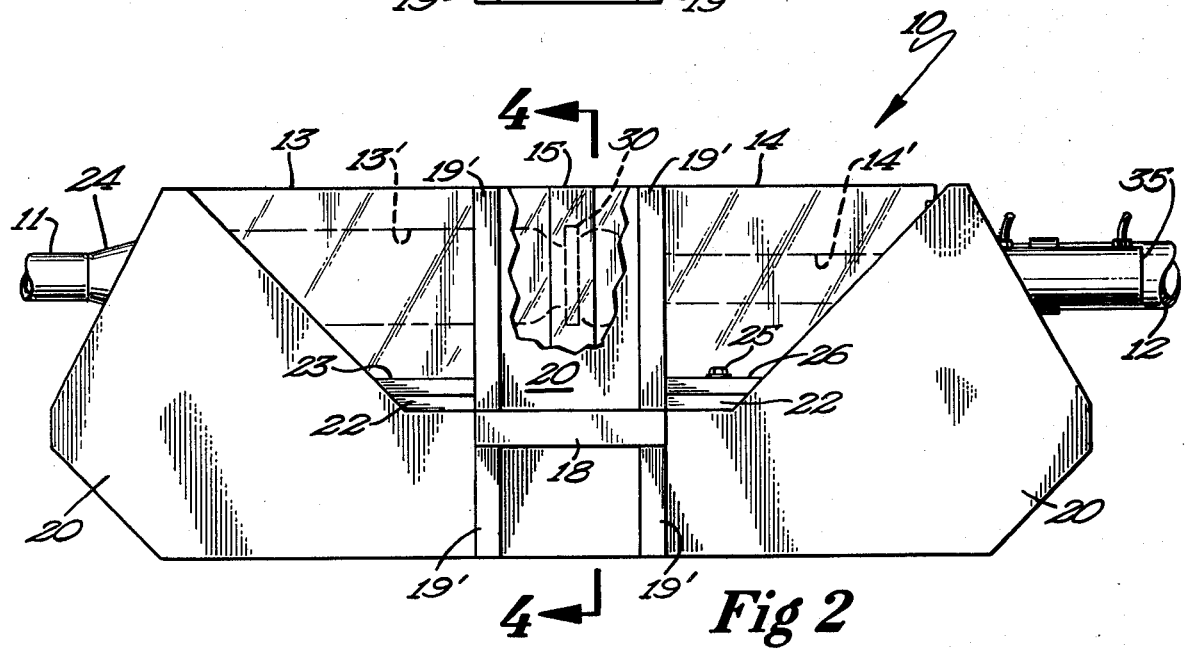
FIG. 2 is a side view of the embodiment of FIG. 1.
Figure 3:
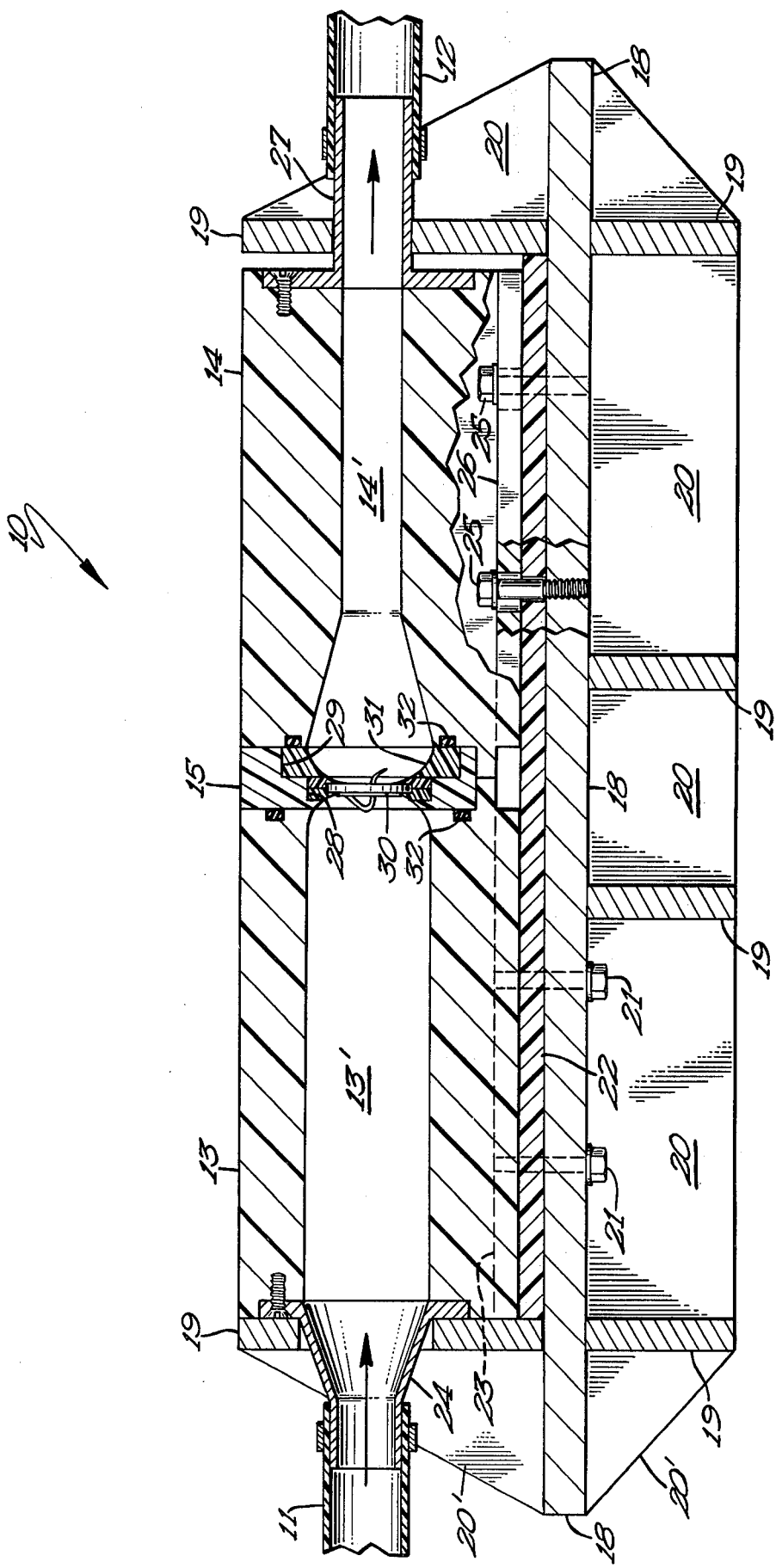
FIG. 3 is a cross section taken along the lines 3—3 in FIG. 1.

The test fixture 10 is formed of chambers 13 and 14 having flow paths 13' and 14' therein (indicated in phantom in FIGS. 1 and 2 and cutaway in FIG. 3). The chambers 13 and 14 are spaced from each other along the system flow channel with their flow paths in communication with the system flow channel.

A shuttle mechanism includes a slide 15 positioned intermediate the chambers 13 and 14, the slide 15 being connected to a rod 16 of an actuable linear motion mechanism 17 as by a threaded connection. The piston mechanism 17 may be any linear motion inducing mechanism, fluid, electric, etc. When activated, the mechanism 17, through the interconnection of the rod 16 with the slide 15, moves the slide 15 between at least first and second positions, for reasons set out more fully below.

Figure 4:
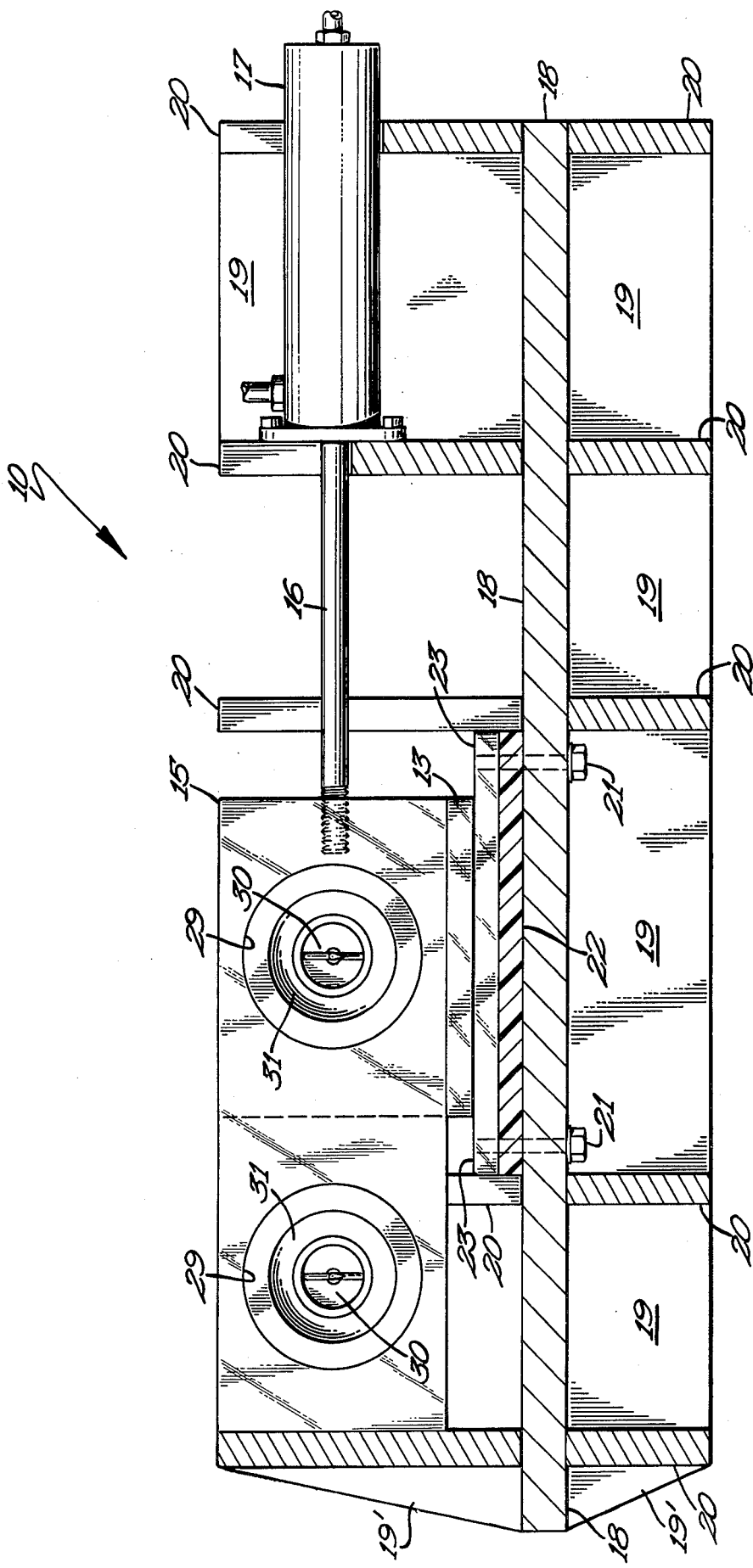
FIG. 4 is a cross section taken along the lines 4—4 in FIG. 2.

In the illustrated embodiment, the components of the test fixture 10 are commonly supported on a plate 18 from which legs 19 and 20 extend (see FIGS. 3 and 4). Bolts 21 extend through an intermediate plate 22 into threaded engagement with a shoulder 23 on chamber 13 (see FIG. 4). An extension of one of the end legs 19 supports an adapter 24, as by a threaded fastener, with that adapter 24 providing fluid communication between that portion 11 of the system fluid channel and the flow path 13' through the chamber 13. Similarly, threaded connectors 25 extend between a shoulder portion 26 of chamber 14 and the plate 18. However, the shoulder 26 of chamber member 14 is provided with elongated slots allowing the chamber member 14 to move relative to the base plate 18, in known manner. An adapter 27, carried by and secured to the chamber member 14 provides fluid communication between the flow path 14' of the chamber 14 and that portion 12 of the system flow channel. Because of the movement of the chamber member 14, to be discussed more fully below, adapter 27 and flow channel portion 12 provide a moving coupling while sealing that coupling, in known manner. Flange extensions 19' and 20' provide extra rigidity in the support of the test fixture components while extensions of two of the legs 20 engage and support the mechanism 17.

As is best illustrated in FIG. 3, the slide 15 is positioned intermediate the chambers 13 and 14 and is provided with a first recess 28 and a second recess 29. The recess 28 is configured to accept a heart valve prosthesis 30 while the recess 29 is configured to receive a collar 31. Recess 29 and collar 31 overlie the recess 28, and the heart valve prosthesis 30 therein, to maintain the prosthesis 30 within the recess 28 during testing. Slide 15 and collar 31 each have a flow aperture concentric with the prosthesis 30 within the recess 28. Those flow apertures may be configured to maintain the desired flow characteristics. Sealing rings 32 surround each of the flow apertures within the slide 15 and collar 31 to facilitate the establishment of a static and dynamic seal between each of the chambers and the slide. Sealing rings 32 may be partially inset in their associated chamber 13 and 14 to facilitate their position maintenance.

With reference to FIG. 1, two heart valve prostheses 30 are illustrated diagrammatically as being supported by the slide 15 with one prosthesis being in alignment with the flow paths 13' and 14' through the chambers 13 and 14, respectively. Movement of the chamber 14 is controlled by linear movement mechanisms 35 which are connected to the chamber 14, in known manner, to induce a linear movement of the chamber 14 on activation, either toward or away from chamber 13. Cylinders 35 may be electrical or fluid operated, in known manner.

In operation, the slide 15 is positioned, via the mechanism 17, such that a heart valve prosthesis 30, that it supports and carries, is positioned within the system flow channel which, in its vicinity, are formed by the flow paths 13' and 14' through the chambers 13 and 14. The mechanism 35 are activated to urge the chamber 14 against the slide 15 and, accordingly, the slide 15 against the chamber 13. In this process, the rings 32 are compressed to establish a static seal around the flow apertures through the collar 31 and slide 15. The flow of desired characteristics may then be established in the flow channel and the prosthesis tested. To remove the prosthesis 30 from the flow channel, the mechanism 35 are again activated to at least ease the pressure between the slide 15 and the chambers 13 and 14. However, the rings 32 should remain somewhat compressed to establish and maintain a dynamic seal. Activation of the mechanism 17 will withdraw the prosthesis from the flow channel and test fixture where it can then be removed from the slide by removal of the collar 31. If a second prosthesis is carried by the slide, movement of the slide to withdraw the first prosthesis may bring the second prosthesis into alignment with the flow channel thereby allowing its testing without an independent test set up. Of course, more than two prostheses may be carried by the slide 15.

Obviously, many modifications and variations of the present invention are possible in light of the above teachings. For example, as noted above, any desired number of prostheses may be carried by the slide 15 for insertion in and withdrawal from a desired orientation within the flow channel flow. When more than one prostheses is carried by the slide 15, it will be most advantageous if it results in proper positioning of one prostheses during removal of another. Also, the chambers 13 and 14 may be of any suitable material. It has been found that Lucite functions well while allowing a viewing of the prosthesis being tested. It is therefore to be understood that, within the scope of the appended claims, the invention may be practiced otherwise than as specifically described.

I claim:

1. In a system for hydrodynamic, in vitro testing of heart valve prostheses of the type having a flow channel and means for including a flow of desired characteristics within said flow channel, said flow channel including test fixture means for supporting a prosthesis to be tested in a desired orientation within said flow, the improvement wherein said test fixture means comprises first and second chamber means spaced from each other along said flow channel and shuttle means intermediate said chamber means and movable between at least first and second positions, said shuttle means comprising means for supporting at least one heart valve prosthesis and selectively positioning said prosthesis in a desired orientation within said flow and without said flow by movement of said shuttle means between said first and second positions.

2. The system of claim 1 wherein said shuttle means comprises means for supporting two heart valve prostheses, said prostheses being alternatively positioned in a desired orientation within said flow by movement of said shuttle means between said first and second positions.

3. The system of claim 2 wherein said shuttle means comprises slide means having a flow aperture for each heart valve prosthesis it supports and means for supporting each prosthesis concentric with its associated flow aperture.

4. The system of claim 3 wherein said supporting means comprises recess means configured to accept a heart valve prosthesis within said slide means.

5. The system of claim 4 wherein said supporting means further comprise removable collar means within said slide means and overlying said recess means, said collar means having a flow aperture cocentric with said slide means flow aperture.

6. The system of claim 5 wherein said collar means lie within further recess means configured to accept said collar means, said further recess means extending from a surface of said slide means to said recess means and being at least co-extensive with said recess means.

7. The system of claim 6 further comprising means for establishing a static and dynamic seal of said flow channel between each of said chamber means and said slide means.

8. The system of claim 7 wherein said seal establishing means comprises compressible means positioned between each of said chamber means and said slide means and surrounding said flow channel and flow apertures when a prosthesis is in said desired orientation.

9. The system of claim 8 wherein said chamber means are movable relative to each other to facilitate movement of said slide mens while maintaining said dynamic seal and to establish said static seal.

10. The system of claim 1 wherein said shuttle means comprises slide means having a flow aperture for each heart valve prosthesis it supports and means for supporting each prosthesis concentric with its associated flow aperture.

11. The system of claim 10 wherein said supporting means comprises recess means configured to accept a heart valve prosthesis within said slide means.

12. The system of claim 11 wherein said supporting means further comprise removable collar means within said slide means and overlying said recess means, said collar means having a flow aperture concentric with said slide means flow aperture.

13. The system of claim 12 wherein said collar means lie within further recess means configured to accept said collar means, said further recess means extending from a surface of said slide means to said recess means and being at least co-extensive with said recess means.

14. The system of claim 13 further comprising means for establishing a static and dynamic seal of said flow channel between each of said chamber means and said slide means.

15. The system of claim 14 wherein said seal establishing means comprises compressible means positioned between each of said chamber means and said slide means and surrounding said flow channel and flow apertures when a prosthesis is in said desired orientation.

16. The system of claim 15 wherein said chamber means are movable relative to each other to facilitate movement of said slide means while maintaining said dynamic seal and to establish said static seal.

17. The system of claim 1 further comprising means for establishing a static and dynamic seal of said flow positioned between each of chamber means and said shuttle means.

18. The system of claim 17 wherein said chamber means are movable relative to each other to facilitate movement of said shuttle means while maintaining said dynamic seal.

* * * * *